(12) United States Patent
McGuigan et al.

(10) Patent No.: US 9,427,447 B2
(45) Date of Patent: *Aug. 30, 2016

(54) ANTI-VIRAL PYRIMIDINE NUCLEOSIDE DERIVATIVES

(71) Applicants: UNIVERSITY COLLEGE CARDIFF CONSULTANTS LIMITED, Cardiff (GB); K.U. LEUVEN RESEARCH AND DEVELOPMENT, Leuven (BE)

(72) Inventors: Christopher McGuigan, Cardiff (GB); Jan Balzarini, Heverlee (BE); Marco Migliore, Cardiff (GB)

(73) Assignees: University College Cardiff Consultants Limited, Cardiff (GB); K.U. Leuven Research and Development, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/482,125

(22) Filed: Sep. 10, 2014

(65) Prior Publication Data

US 2015/0072948 A1 Mar. 12, 2015

Related U.S. Application Data

(63) Continuation of application No. 13/690,794, filed on Nov. 30, 2012, now Pat. No. 8,859,512, which is a continuation of application No. 12/226,044, filed as application No. PCT/GB2007/001677 on May 9, 2007, now Pat. No. 8,329,664.

(30) Foreign Application Priority Data

May 9, 2006 (GB) .................................. 0609178.9

(51) Int. Cl.
*A01N 43/04* (2006.01)
*A61K 31/70* (2006.01)
*A61K 31/7068* (2006.01)
(Continued)

(52) U.S. Cl.
CPC ......... *A61K 31/7068* (2013.01); *C07D 487/04* (2013.01); *C07D 491/04* (2013.01); *C07D 495/04* (2013.01); *A61K 31/706* (2013.01); *A61K 31/7052* (2013.01); *A61K 31/7064* (2013.01)

(58) Field of Classification Search
None
See application file for complete search history.

(56) References Cited

U.S. PATENT DOCUMENTS 5,430,026 A 7/1995 Hertel et al.
6,444,682 B1 9/2002 Simmonds et al.
(Continued)

FOREIGN PATENT DOCUMENTS

EP 346108 A2 12/1989
JP 62-255499 A 11/1987
(Continued)

OTHER PUBLICATIONS

Angell, A. et al., "Bicyclic anti-VZV nucleosides: thieno analogues bearing an alkylphenyl side chain have reduced antiviral activity", *Bioorganic & Medicinal Chemistry Letters*, 14(10):2397-2399 (2004).
(Continued)

*Primary Examiner* — Patrick Lewis
(74) *Attorney, Agent, or Firm* — Cooley LLP; Ivor R. Elrifi; Heidi A. Erlacher

(57) ABSTRACT

A compound for use in the treatment or prophylaxis of viral infections such, for example as chicken pox or shingles caused by the Varicella Zoster virus, said compound having the general formula (II): wherein X is O, S, NH or $CH_2$, Y is O, S or NH, Z is O, S or $CH_2$, $R_1$ is $C_{1-6}$ alkyl, preferably n-alkyl, e.g., n-pentyl or n-hexyl, and one of $R_2$ and $R_3$ is OH, and the other of $R_3$ and $R_2$ is a neutral, non-polar amino acid moiety, or a pharmaceutically acceptable salt or hydrate thereof. Said neutral, non-polar amino acid moiety $R_2$ or $R_3$ may be (IV): in which $R_4$, $R_5$, $R_6$ and $R_7$ are each independently H or $C_{1-2}$ alkyl. In preferred embodiments, one of $R_2$ or $R_3$ is valine, leucine, isoleucine or alanine, particularly valine.

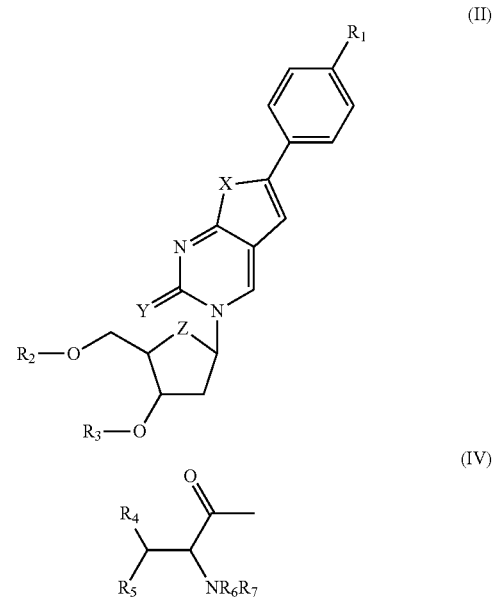

11 Claims, 1 Drawing Sheet

(51) Int. Cl.
C07D 487/04 (2006.01)
C07D 491/04 (2006.01)
C07D 495/04 (2006.01)
A61K 31/706 (2006.01)
A61K 31/7064 (2006.01)
A61K 31/7052 (2006.01)

(56) References Cited

U.S. PATENT DOCUMENTS

| | | |
|---|---|---|
| 6,455,513 B1 | 9/2002 | McGuigan et al. |
| 6,573,247 B1 | 6/2003 | McGuigan et al. |
| 7,419,968 B1 | 9/2008 | Shepard |
| 7,585,851 B2 | 9/2009 | Bryant et al. |
| 2001/0018440 A1 | 8/2001 | Chu et al. |
| 2003/0148967 A1 | 8/2003 | McGuigan et al. |
| 2003/0176370 A1 | 9/2003 | McGuigan et al. |
| 2004/0266996 A1 | 12/2004 | Rabi |
| 2005/0137141 A1 | 6/2005 | Hilfinger |
| 2008/0070852 A1 | 3/2008 | Averett et al. |

FOREIGN PATENT DOCUMENTS

| | | |
|---|---|---|
| WO | WO 01/07087 A2 | 2/2001 |
| WO | WO 01/07454 A1 | 2/2001 |
| WO | WO 01/96353 A3 | 4/2002 |
| WO | WO 2004/002999 A8 | 2/2005 |

OTHER PUBLICATIONS

Brancale, A. et al., "Synthesis and anti-varicella-zoster virus activity of some novel bicyclic nucleoside inhibitors; effect of enhanced aqueous solubility", *Antiviral Chem. Chemother*, 11(6):383-393 (2000).
Crisp, G.T. et al., "Palladium-catalyzed coupling of terminal alkynes with 5-(trifluoromethanesulfonyloxy) pyrimidine nucleosides", *J. Org. Chem.*, 58(24):6614-6619 (1993).
Cruickshank, K.A. et al., "Oligonucleotide Labelling: A Concise Synthesis of a Modified Thymidine Phosphoramidite", *Tetra. Lett.*, 29(41):5221-5224 (1988).
De Clercq et al., "Antiviral Drugs in Current Clinical Use", *Journal of Clinical Virology*, 30:115-133 (2004).
De Clercq, E. et al., "Nucleic acid related compounds. 4~. Synthesis and biological activities of 5-alkynyluracil nucleosides", J. Med. Chem., 26(5):661-666 (1983).
De Clercq, E. et al., "(E)-5-(2-Bromovinyl)-2'-deoxyuridine: A potent and selective anti-herpes aged", *Proc. Natl. Acad. Sci.*, 76(6):2947-2951 (1979).
Good et al., "Disposition in the dog and the rat of 2,6-diamino-9-(2-hydroxyethoxymethyl)purine (A134U), a potential prodrug of acyclovir", *J. Pharmacol. Exp. Ther.*, 227:644-651 (1983).
Inoue et al., "Synthesis of Dodecadeoxynucleotides Containing a Pyrrolo[2,3-d]-pyrimidine Nucleoside and Their Base-pairing Ability", *Nippon Kagaku Kaishi (J. Chem. Soc. Japan, Chemistry and Industrial Chemistry)*, 7:1214-1220 (Jul. 1987); Chemical Abstracts, 108, Abstract No. 187183a (May 23, 1988).
Jung et al., "Single-dose pharmacokinetics of valaciclovir in HIV- and CMV-seropositive subjects", *The Journal of Clinical Pharmacology*, 39:800-804 (1999).

Kerr, C.E. et al., "Synthesis of N, N-dialkylaniline-2'-deoxyuridine conjugates for DNA-mediated electron transfer studies", *Nucleosides, Nucleotides, Nucleic Acids*, 19(5&6):851-866 (2000).
Krenitsky et al., "6-Deoxyacyclovir: a xanthine Oxidase-activated prodrug of acyclovir", *Proc. Natl. Acad. Sci.*, 81:3209-3213 (1984).
Kumar, R. et al., "Synthesis and Properties of 5-(1, 2-Dihaloethyl)-2'-deoxyuridines and Related Analogues", *J. Heterocyclic Chem.*, 28:1917-1925 (1991).
Kumar, R. et al., "Synthesis of 5-(1-azidovinyl) and 5-{2-(1-aziriny1)] analogs of 2'-deoxyuridine", *Can. J. Chem.*, 74:1609-1615 (1996).
Malakhova, E.V. et al., "Reagents for Introducing a Fluorescent Deoxyuridine 2-Phenylbenzoxazole Derivative into Oligonucleotides", *Biiorg. Khim.*, 24(9):688-695 (1998).
Malakhova, E.V., et al., "Reagents for introducing a fluorescent deoxyuridine 2-phenylbenzoxazola derivative into oligonucleotides", *Bioorg. Khim.*, 24(9):688-695 (1998) (Chemical Abstract No. 130:352490, (2 pages).
McGuigan, C. et al., "Phosphoramidate derivatives of d4T with improved anti-HIV efficacy retain full activity in thymidine kinase-deficient cells", *Bioorganic & Medicinal Chemistry Letters*, 6(10):1183-1186 (1996).
McGuigan et al., "Preclinical Development of the BCNA's: The Most Potent Anti-VZV Agents Reported to Date", Abstract 14, p. A31, from Program and Abstracts from the Nineteenth International Conference on Antiviral Research, May 7-11, 2006, Antiviral Research 70, A1-A99 (2006).
McGuigan, C. et al., "Highly Potent and Selective Inhibition of Varicella-Zoster Virus by Bicyclic Furopyrimidine Nucleosides Bearing an Aryl Side Chain", *J. Med. Chem.*, 43(26):4993-4997 (2000).
McGuigan, C. et al., "Potent and Selective Inhibition of Varicella-Zoster Virus (VZV) by Nucleoside Analogues with Unusual Bicyclic Base", *J. Med. Chem.*, 42(22):4479-4484 (1999).
Morvan et al., "α-Oligodeoxynucleotides Containing 5-Propynyl Analogues of α-Deoxyuridine and α-Deoxycytidine: Synthesis and Base Pairing Properties", *Tetrahedron*, 54(1/2):71-82 (1998).
Robins, M.J. et al., "Nucleic Acid Related Compounds. 31. Smooth and Efficient Palladium-Copper Catalyzed Coupling of Terminal Alkynes with 5-Iodouracil Nucleosides", *Tetra. Lett.*, 22:421-424 (1981).
Robins, M.J. et al., "Nucleic acid related compounds. 39. Efficient conversion of 5-iodo to 5-alkynyl and derived 5-substituted uracil bases and nucleosides", *J. Org. Chem.*, 48(11):1854-1862 (1983).
Silverman, R., The Organic Chemistry of Drug Design and Drug Action, "Chapter 8: Pro drugs and Drug Delivery Systems", Published 1992 by Academic Press, pp. 352-397.
Tolstikov et al., "New Type of Reaction of 5-Iodopyrimidine Nucleosides with Alkynes", Izv. Akad. Nauk, Ser. Khim., (Issue No. 3), 596-598 (1993); Chemical Abstracts, 124(7):1379, Abstract No. 87652q (Feb. 12, 1996).
Tolstikov et al., "Novel Type of Interaction of 5-Iodopyrimidinonucleosides with Alkynes", Izv. Akad. Nauk, Ser. Khim., (Issue No. 6), 1449-1450 (1992); Chemical Abstracts, 118(13), p. 855, Abstract No. 124938m (Mar. 29, 1992).
Weller et al., "Pharmacokinetics of the acyclovir pro-drug valaciclovir after escalating single-and multiple-dose administration to normal volunteers", *Clinical Pharmacology and Therapeutics*, pp. 595-605 (1993).
Woo, J. et al., "G/C-modified oligodeoxynucleotides with selective complementarity: synthesis and hybridization properties", *Nucl. Acids Res.*, 24(13):2470-2475 (1996).

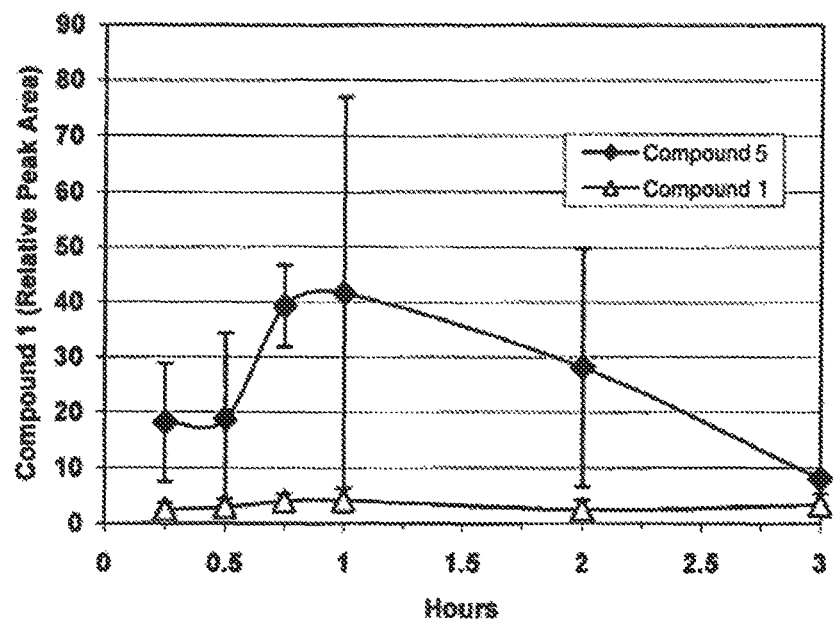

ANTI-VIRAL PYRIMIDINE NUCLEOSIDE DERIVATIVES

RELATED APPLICATIONS

This is a continuation of U.S. patent application Ser. No. 13/690,794, filed Nov. 30, 2012, which is a continuation of U.S. patent application Ser. No. 12/226,044, filed Dec. 21, 2009, which is a national stage application, filed under 35 U.S.C. 371, of International Application No. PCT/GB2007/001677, filed May 9, 2007, which claims the benefit of GB Serial No. 0609178.9, filed May 9, 2006.

The present invention relates to ester derivatives of certain nucleoside analogues having therapeutic use in the prophylaxis and treatment of viral infections such, for example, as those caused by the Varicella Zoster virus (WV). Varicella Zoster virus is the aetiological agent in chickenpox and shingles, which can cause considerable human illness and suffering. The invention also provides a pharmaceutical composition comprising such an ester derivative, and a method of treatment or prophylaxis of viral infection by administering such a derivative.

WO 01/83501 A1, the contents of which are incorporated herein by reference, describes certain nucleoside analogues with potent activity against Varicella Zoster virus (VZV), said nucleoside analogues having general formula (I):

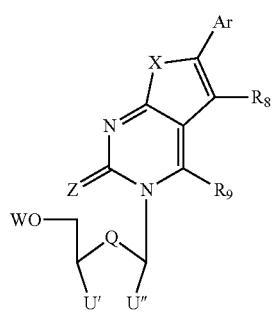

(I)

wherein:

Ar is an optionally substituted, aromatic ring system, the aromatic ring system comprising one six-membered aromatic ring or two fused six-membered aromatic rings;

$R_8$ and $R_9$ are each independently selected from the group comprising hydrogen, alkyl, cycloalkyl, halogens, amino, alkylamino, dialkylamino, nitro, cyan, alkyoxy, aryloxy, thiol, alkylthiol, arythiol, aryl;

Q is selected front the group comprising O, S and $CY_2$, where Y may be the same or different and is selected from H, alkyl and halogens;

X is selected from the group comprising O, NH, S, N-alkyl, $(CH_2)$, where m is 1 to 10, and $CY_2$ where Y may be the same or different and is selected from hydrogen, alkyl and halogens;

Z is selected from the group comprising O, S, NH, and N-alkyl;

U" is H and U' is selected front H and $CH_2T$, or U' and U" are joined so as to form a ring moiety including Q wherein U'-U" together is respectively selected from the group comprising CTH-CT'T" and CT'=CT', so as to provide ring moieties selected from the group comprising:

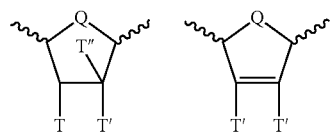

wherein T is selected from the group comprising OH, H, halogens, O-alkyl, O-acyl, O-aryl, CN, $NH_2$ and $N_3$;

T' is selected from the group comprising H and halogens and, where more than one T' is present, they may be the same or different;

T" is selected from the group comprising H and halogens; and

W is selected from the group comprising H, a phosphate group and a pharmacologically acceptable salt, derivative or prop-drug thereof;

with the proviso that when T is OAc and T' and T" are present and are H, Ar not 4-(2-benzoaxazolyl)phenyl.

Compounds 1 and 2 below are particularly preferred compounds according to WO 01/83501 A1:

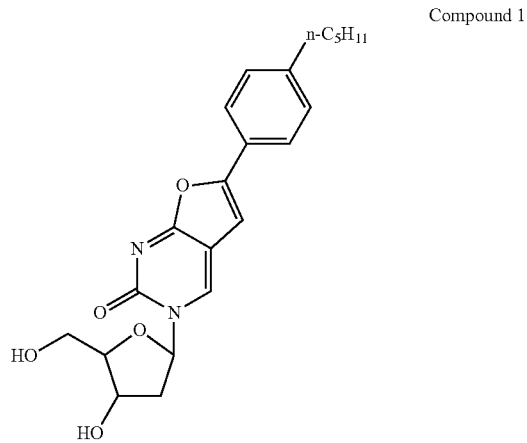

Compound 1

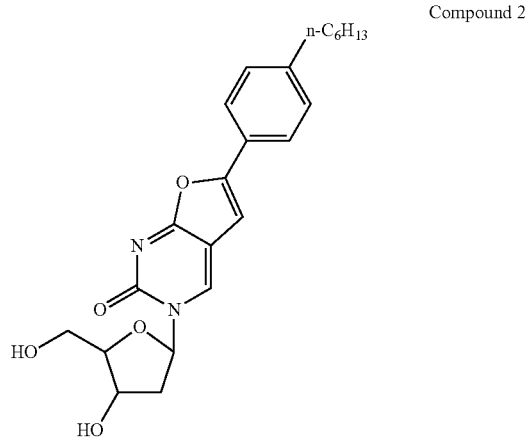

Compound 2

BRIEF DESCRIPTION OF THE DRAWINGS

FIG. 1: a graph of Mean±SD Plasma Compound 1 (shown as relative peak area) in Female Mice After a Single Oral Gavage Dose of Compound 1 (25 mg/kg) or Compound 5 (31.25 mg/kg, equivalent to 25 mg/kg of Compound 1).

An object of the present invention is to provide novel compounds for the treatment or prophylaxis of viral infections, especially those caused or exacerbated by the Varicella Zoster virus (VZV).

Another object of the present invention is to provide compounds for the treatment of such viral infections, said compounds having improved bioavailabilities.

Yet another object of the present invention is to provide such compounds which have advantageous pharmacokinetic properties.

A different object of the present invention is to provide a method of making such compounds.

According to one aspect of the present invention therefore there is provided a compound of general formula (II):

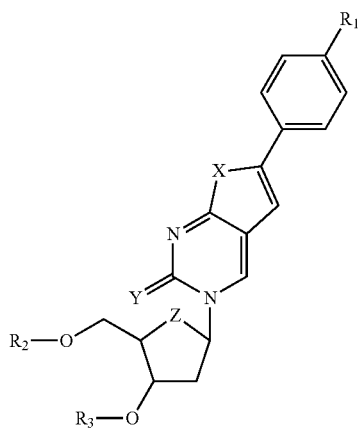

wherein X is O, S, NH or CH$_2$,
Y is O, S or NH,
Z is O, S or CH$_2$,
R$_1$ is C$_{1-6}$ alkyl, preferably n-alkyl, e.g., n-pentyl or n-hexyl, and
one of R$_2$ and R$_3$ is OH, and the other of R$_3$ and R$_2$ is a neutral, non-polar amino acid moiety,
or a pharmaceutically acceptable salt or hydrate thereof.

Preferably said neutral, non-polar amino acid moiety R$_2$ or R$_3$ is:

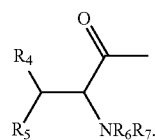

in which R$_4$, R$_5$, R$_6$ and R$_7$ are each independently H or C$_{1-2}$ alkyl.

R$_6$ and R$_7$ are preferably both H.

In some embodiments, one of R$_2$ or R$_3$ may be valine, leucine, isoleucine or alanine. Preferably R$_2$ or R$_3$ is valine.

It is to be understood that the valine ester of the present invention may be either L-valine, D-valine or D,L-valine.

Further, X, Y and Z are preferably all O.

Particularly preferred compounds according to the present invention are

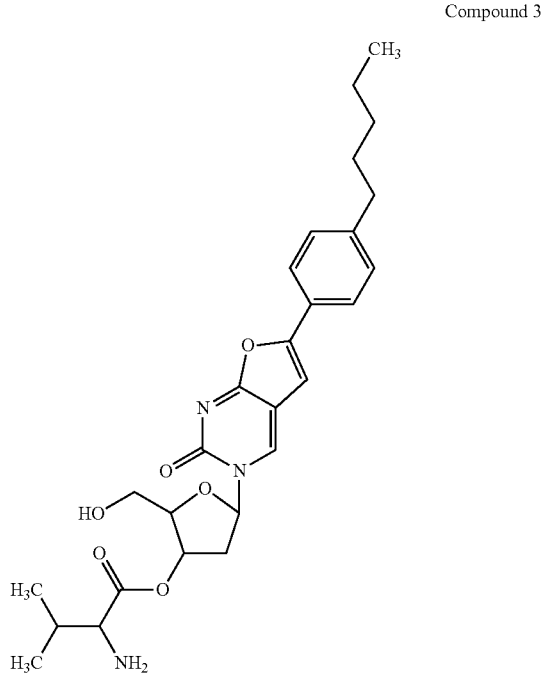

Compound 3

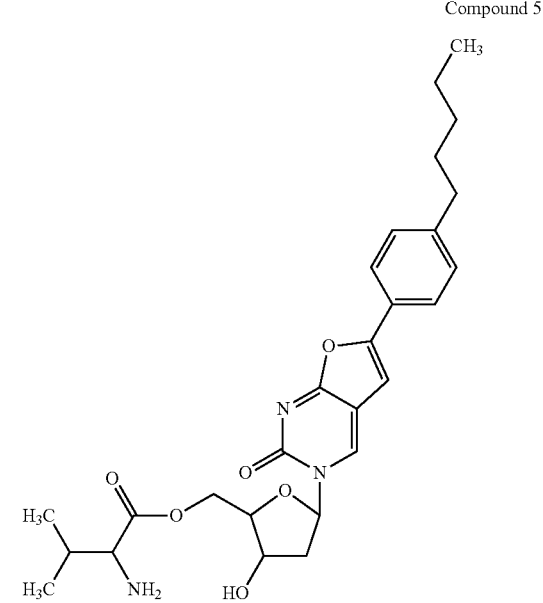 [SMILES: CCCCCc1ccc(-c2cc3cn(C4CC(O)C(COC(=O)C(N)C(C)C)O4)c(=O)nc3o2)cc1]

Compound 5

It will be appreciated that Compounds 3 and 5 are the valine esters of the 3'- and 5'-hydroxy groups respectively of Compound 1.

According to a different aspect of the present invention there is provided a method of synthesising a compound of the invention, said method comprising esterifying a compound of formula (III):

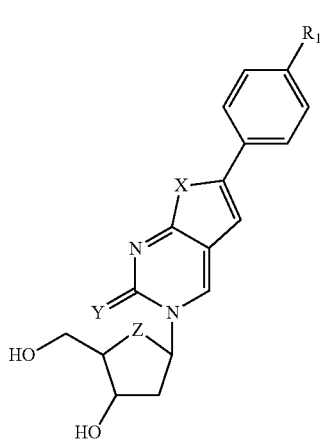

with a protected neutral, non-polar amino acid, wherein $R_1$, X, Y and Z are as defined above.

Preferably, said amino acid has the formula (IV):

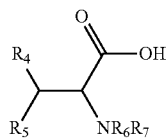

wherein $R_4$, $R_5$, $R_6$ and $R_7$ are as defined above.

The α-amino group is suitably protected during the esterification reaction. In some embodiments, where $R_6$ and $R_7$ are both H, said amino acid may be protected using a 3.9-fluorenylmethoxycarbonyl (Fmoc) protecting group. Other suitable protecting groups are known and available to those skilled in the art.

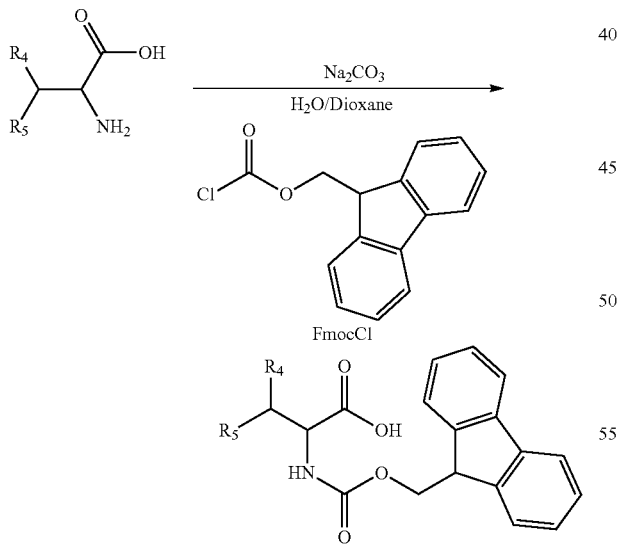

The Fmoc group may be introduced under Schotten-Baumen conditions. It is exceptionally stable towards acid. The cleavage of this group may be base catalysed (ammonia, piperidine, morpholine, DBU) undergoing an E1 β-elimination mechanism.

The esterification is preferably carried out under Mitsunobu conditions[1]:

[1] Mitsunobu, Synthesis, January 1981: 1-28

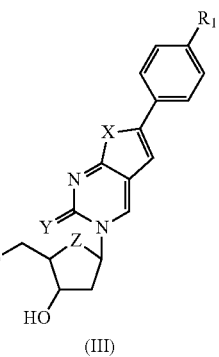

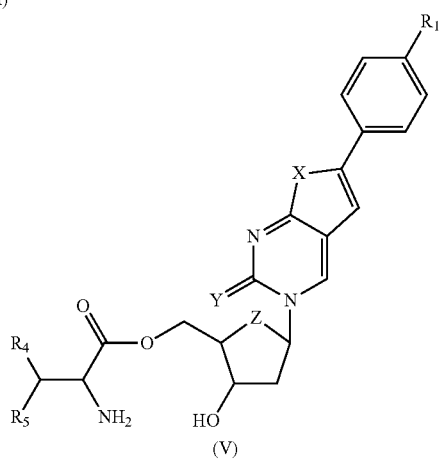

The hydrochloride salt may be prepared by treatment of the ester (V) with a solution of HCl in THF.

Preferably, $R_1$ is n-pentyl, X, Y and Z are all O, and $R_4$ and $R_5$ are both methyl.

It has been found that the compounds of the present invention, and their hydrochloride salts, e.g., Compound 6 (see below), have advantageous pharmacokinetic (PK) properties and improved bioavailability as compared to Compound 1 of WO 01/83501 A1.

Compound 6

Bioavailability is often a key factor in the practical application of a drug as a therapeutic agent and compounds that demonstrate enhanced PK and/or solubility generally have improved potency in vivo over compounds with less favorable PK properties even though their in vitro potency may be similar. Such compounds, i.e., derivatives of known in vitro active compounds, are often referred to as prodrugs. Novel Compound 5 and its hydrochloride salt Compound 6, are examples of two such prodrugs.

Compounds 5 and 6 were tested for antiviral activity as described below and found to be active. In addition, a comparative study of the pharmacokinetic behaviour of Compounds 1 and 5 was conducted in a mouse model, demonstrating the improved bioavailability of Compound 5 compared to Compound 1.

According to another aspect of the present invention therefore there is provided a compound according to the present invention for use in a method of treatment, particularly the prophylaxis or treatment of a viral infection. In some embodiments, said compound may be provided for use in the treatment or prophylaxis of an infection with the Varicella Zoster virus.

According to a yet another aspect of the present invention there is provided use of a compound according to the present invention in the manufacture of a medicament for the prophylaxis or treatment of viral infection, especially a viral infection caused by the Varicella Zoster virus, e.g., chicken pox or shingles.

According to yet another aspect of the present invention there is provided a method of prophylaxis or treatment of viral infection, said method comprising administration to a human or non-human animal patient in need of such treatment an effective dose of a compound according to the present invention.

According to a thither aspect of the present invention there is provided a pharmaceutical composition comprising a compound of the present invention in combination with a pharmaceutically acceptable excipient. Medicaments embodying the present invention can be administered by oral, enteral or parenteral routes, including intravenous, intramuscular, intraperitoneal, subcutaneous, transdermal, airway (aerosol), rectal, vaginal and topical (including buccal and sublingual) administration.

For oral administration, compounds embodying the present invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include bard gelatin capsules which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, compounds embodying the present invention will generally be provided in sterile aqueous solutions or suspensions, buffered to an appropriate pH and isotonicity. Suitable aqueous vehicles include Ringer's solution and isotonic sodium chloride. Aqueous suspensions embodying the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Compounds embodying the present invention can be presented as liposome formulations.

In general, a suitable dose will be in the range of 0.001 to 300 mg per kilogram body weight of the recipient per day, preferably in the range of 0.01 to 25 mg per kilogram body weight per day and most preferably in the range 0.05 to 10 mg per kilogram body weight per day. The desired dose is preferably presented as two, three, four, five or six or more sub-doses administered at appropriate intervals throughout the day. These sub-doses may be administered in unit dosage forms, for example, containing 0.1 to 1500 mg, preferably 0.2 to 1000 mg, and most preferably 0.5 to 700 mg of active ingredient per unit dosage form.

Following are various examples of the invention with reference to the accompanying drawings, from which examples further advantages and effects of the compounds of the invention will be apparent.

In the drawings the single FIGURE is a graph of Mean±SD Plasma Compound 1 (shown as relative peek area) in Female Mice After a Single Oral Gavage Dose of Compound 1 (25 mg/kg) or Compound 5 (31.25 mg/kg, equivalent to 25 mg/kg of Compound 1)

EXPERIMENTAL PROCEDURES AND BIOLOGICAL RESULTS

Preparation of Compounds

Example 1

Preparation of Compound 5

Formation of Valine Ester

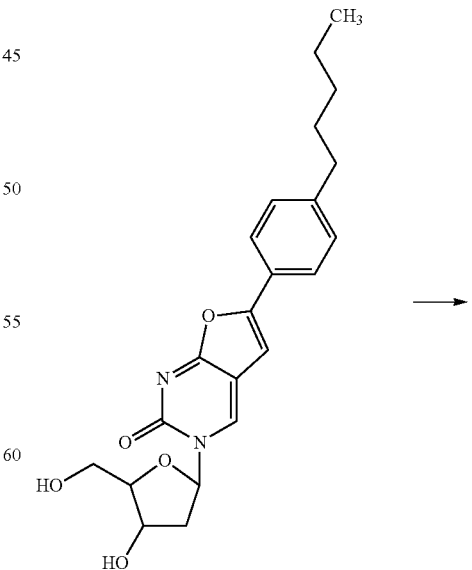

Compound 1

-continued

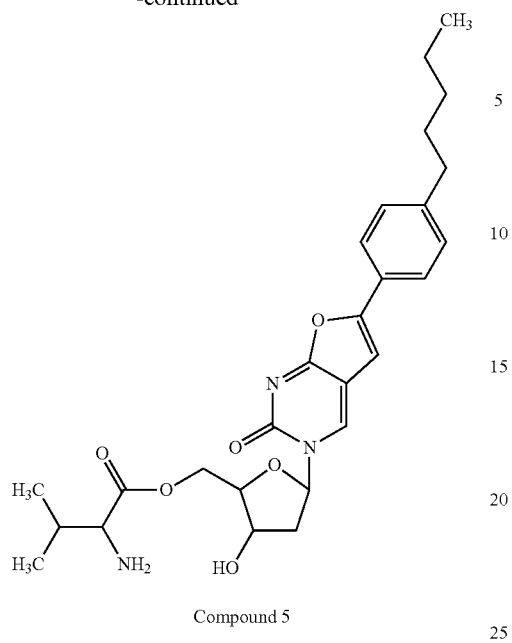

Compound 5

Compound 1 (200 mg, 0.5 mmol, prepared as described in WO 01/83501 A1, Example 3, page 15) was dissolved in dry DMF (5 mL), followed by the addition of polymer-bound triphenylphosphine [370 mg, 1.1 mmol, (3 mmol p/g resin)] and di-tert-butyl azodicarboxylate (DBAD) (231 mg, 1.0 mmol) to the mixture and stirred for 20 minutes. A solution of Fmoc-Val-OH (340 mg, 1.0 mmol) in DMF (5 mL) was added dropwise over a period of 30 minutes. The reaction mixture was stirred at room temperature under an argon atmosphere until complete disappearance of the starting material (overnight). The resin was filtered off and washed with ethyl acetate. Piperidine (1 mL, 10 mmol) was added to the solution and stirred for 10 minutes. The solvent was removed under reduced pressure without warming over 35° C. and the residue was dissolved in ethyl acetate (20 mL), washed with 10% $NaHCO_3$ (3×20 mL) and brine (2×20 mL). The final residue was purified by column chromatography (gradient $CH_2Cl_2$:MeOH 100% 98% 95% 90%), to give 137 mg of Compound 5 (55% yield) as a yellow solid.

$^1$H-NMR ($CDCl_3$) δ: 8.3 (1H, s), 7.55 (2H, d), 7.15 (2H, d), 6.6 (1H, s), 6.25 (1H, t), 4.45-4.30 (4H, m), 3.23 (1H, d), 2.80 (1H, m), 2.53 (2H, t), 2.12 (1H, m), 1.97 (1H, m), 1.60 (2H, m), 1.24 (4H, m), 0.90-0.78 (9H, m).

$^{13}$C-NMR ($CDCl_3$) δ: 175.16, 171.62, 156.26, 154.89, 145.19, 135.29, 129.02, 125.69, 124.95, 108.60, 96.82, 88.73, 85.08, 70.90, 64.19, 60.19, 41.91, 35.82, 32.32, 31.44, 30.89, 22.50, 19.30, 17.24, 13.99.

Example 2

Preparation of Compound 6

Formation of the HCl Salt

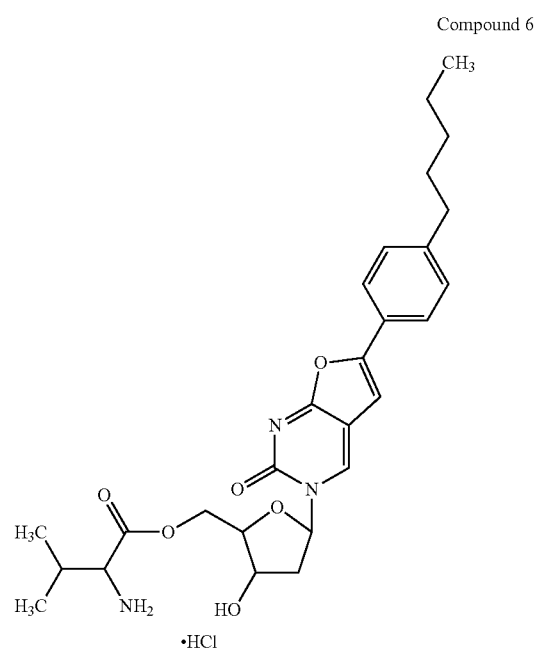 [SMILES: CCCCCc1ccc(-c2cc3cn(C4CC(O)C(COC(=O)C(N)C(C)C)O4)c(=O)nc3o2)cc1 ; Cl]

Compound 6

300 mg of Compound 5 were dissolved in 3 mL of THF. Under vigorous stirring 2 mL of HCl 1M were added at 0° C. and the mixture were stirred for 10 minutes. The solvents were dried under reduce pressure to obtain 322 mg (100%) of yellow oil that solidified with addition of ether.

$^1$H-NMR ($d_6$-DMSO) δ: 8.6 (4H, bs), 7.70 (2H, d), 7.30 (2H, d), 7.20 (1H, s), 6.22 (1H, t), 5.60 (1H, bs), 4.48 (2H, m), 4.30 (1H, m), 4.16 (1H, m), 3.98 (1H, m), 2.61 (2H, t), 2.44 (1H, m), 2.25 (1H, m), 2.18 (1H, m), 1.57 (2H, m), 1.32 (4H, m), 1.00-0.83 (9H, m).

$^{13}$C-NMR ($d_6$-DMSO) δ: 171.13, 168.88, 153.97, 153.70, 144.18, 137.94, 129.04, 125.77, 124.58, 107.22, 98.75, 87.71, 84.13, 69.73, 65.26, 57.35, 40.18, 34.88, 30.88, 30.39, 29.38, 21.91, 18.26, 17.55, 13.90.

Biological and Pharmacokinetic Studies

In order to demonstrate the improved exposure profile of Compound 5, several experiments were run using mouse animal models. Below are representative results

Pilot Comparative Virology Study with Compounds 1 and 5

The objective of this pilot study was to compare the antiviral activity of Compounds 1 and 5 in HEL cells inoculated with the thymidine-kinase deficient Oka VZV strain. Antiviral activity was assessed as the ability of 1 or 5 to reduce viral plaque formation after incubation periods ranging from 3 to 7 days compared to untreated control cultures. Preliminary results of the antiviral efficacy studies showing comparable efficacy between the two compounds are shown in Table 4.2.

TABLE 1

Preliminary Results Comparing Compound 1 and Compound 5 for Anti-Varicella Zoster Virus Activity in HEL Cells

| Compound | $EC_{50}$ in VZV OKA |
|---|---|
| 1 | 0.007 μM (2.8 ng/mL) |
| 5 | 0.016 μM (8.0 ng/mL) |

Note:
The molecular weight of Compound 5 is approximately 1.25 times that of Compound 1 due to the valine ester.

In conclusion, the results of these comparative pilot in vitro studies showed that Compound 5 has comparable in vitro antiviral activity to Compound 1.

Nonclinical Pharmacokinetic Studies with Compound 5

A pilot study was conducted with Compounds 1 and 5 to compare the relative bioavailability of Compound 1 after oral dosing in mice. Two groups of female mice received equimolar doses of Compound 1 (25 mg/kg) or 5 (31.25 mg/kg; equivalent to 25 mg/kg of Compound 1) as a single oral gavage dose) formulated in 0.5% carboxymethylcellulose. The mice were serially sacrificed at time-points ranging from 0.25 to 3 hours post dosing (3 mice/time-point), and plasma samples were taken and analyzed for Compound 1 concentration using a non-validated HPLC method with fluorescence detection. Results are reported as relative peak areas for Compound 1, which assumes that peak area is directly proportional to concentration over these ranges of concentrations.

The results of this study are shown in the accompanying FIGURE. Plasma concentrations of Compound 1 were much higher in mice receiving Compound 5 compared to mice receiving Compound 1. Note that although these data do not provide absolute plasma concentrations of Compound 1, one can estimate from the peak areas that Compound 5 increases the oral bioavailability of Compound 1 by approximately 8.4 to 10 fold (e.g., the AUC is increased by ~840% and the $C_{max}$ is increased by ~1000%).

In conclusion, this data supports the hypothesis that Compound 5 is a prodrug of Compound 1, and greatly increases the oral bioavailability of Compound 1.

What is claimed:

1. A pharmaceutical composition comprising a compound selected from:

Compound 3 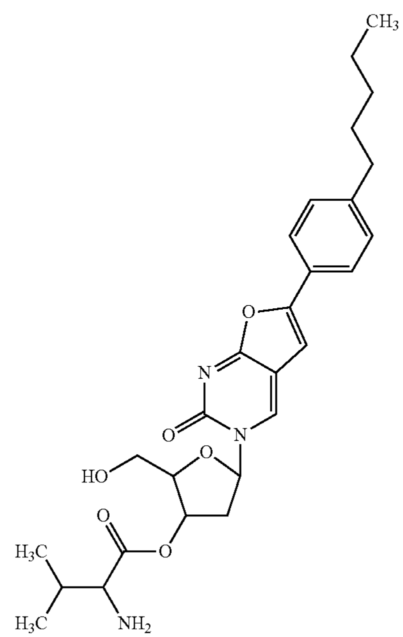 and

Compound 5 or a pharmaceutically acceptable salt or hydrate thereof, and a pharmaceutically acceptable excipient.

2. The pharmaceutical composition of claim 1, wherein the compound is:

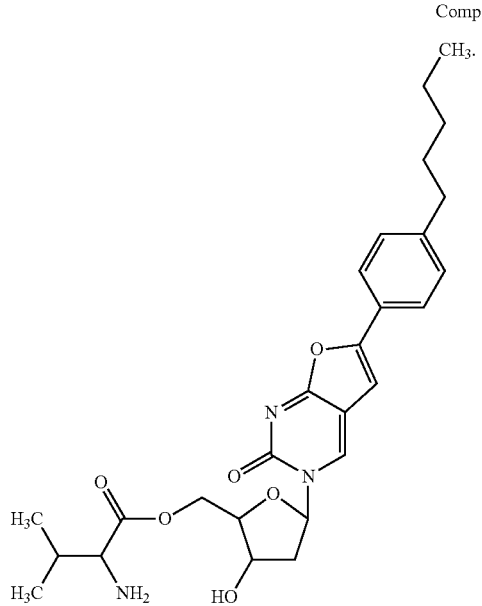

Compound 5

3. The pharmaceutical composition of claim 1, wherein the compound is:

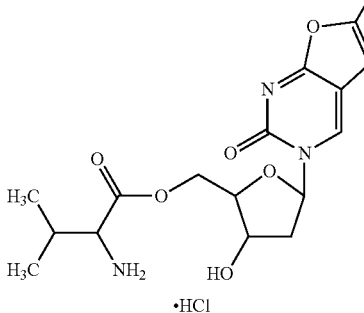

Compound 6

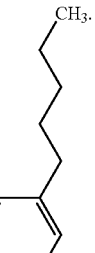

·HCl

4. A method of prophylaxis or treatment of a viral infection, comprising administering to a human or non-human animal patient in need thereof the pharmaceutical composition of claim 1.

5. The method of claim 4, wherein the viral infection is caused by Varicella Zoster virus.

6. The method of claim 5, wherein the viral infection is chicken pox or shingles.

7. The method of claim 4, wherein the patient is a human.

8. The method of claim 4, wherein the compound is administered by an oral, enteral or parenteral route.

9. The method of claim 8, wherein the compound is administered by an intravenous, intramuscular, intraperitoneal, subcutaneous, transdermal, airway, rectal, vaginal, or topical route.

10. The method of claim 4, wherein the compound is administered at a dose of 0.001 to 300 mg per kilogram body weight of the recipient per day.

11. The method of claim 10, wherein the dose is administered as two, three, four, five, or six more sub-doses, wherein said sub-doses are administered at appropriate intervals throughout the day.

* * * * *